US010548575B2

(12) United States Patent
Harris et al.

(10) Patent No.: US 10,548,575 B2
(45) Date of Patent: Feb. 4, 2020

(54) DEVICES, SYSTEMS, AND METHODS FOR ORAL AND NON-ORAL EXAMINATION AND DIAGNOSIS

(71) Applicant: GlobalMedia Group, LLC, Scottsdale, AZ (US)

(72) Inventors: Michael D. Harris, Scottsdale, AZ (US); Joel E. Barthelemy, Paradise Valley, AZ (US)

(73) Assignee: GlobalMedia Group, LLC, Scottsdale, AZ (US)

( * ) Notice: Subject to any disclaimer, the term of this patent is extended or adjusted under 35 U.S.C. 154(b) by 184 days.

(21) Appl. No.: 15/675,506

(22) Filed: Aug. 11, 2017

(65) Prior Publication Data
US 2019/0046168 A1 Feb. 14, 2019

(51) Int. Cl.
*A61B 13/00* (2006.01)
*A61B 5/00* (2006.01)
*A61B 1/267* (2006.01)

(52) U.S. Cl.
CPC .............. *A61B 13/00* (2013.01); *A61B 1/267* (2013.01); *A61B 1/2673* (2013.01); *A61B 1/2676* (2013.01); *A61B 5/4552* (2013.01)

(58) Field of Classification Search
CPC ....... A61B 13/00; A61B 5/4552; A61B 1/267; A61B 1/2673; A61B 1/2676
See application file for complete search history.

(56) References Cited

U.S. PATENT DOCUMENTS

| 5,825,502 | A | 10/1998 | Mayer |
| 5,990,942 | A | 11/1999 | Ogino |
| 6,262,763 | B1 | 7/2001 | Totsuka et al. |
| 8,814,897 | B1* | 8/2014 | Schultz ............... A61B 1/24 606/185 |
| 2003/0069752 | A1 | 4/2003 | LeDain et al. |
| 2006/0064319 | A1 | 3/2006 | Loevner |
| 2008/0177148 | A1* | 7/2008 | Chen ................. A61B 1/267 600/188 |
| 2009/0189972 | A1 | 7/2009 | Harris et al. |

* cited by examiner

*Primary Examiner* — Christian A Sevilla
(74) *Attorney, Agent, or Firm* — Snell & Wilmer L.L.P.

(57) ABSTRACT

An examination device for use with a mobile device comprises a housing removably coupled to the mobile device. The housing may be coupled to the mobile device by a rear surface, opposing side surfaces, a top surface, and a retention lip that extends over the front of the mobile device. A retention structure may be mechanically coupled to the housing and may also define a rectangular slot. A tongue depressor may be retained by the retention structure and may also extend away from the rectangular slot. A cutaway may be defined by a wall of the housing. The cutaway may be positioned on the housing to expose a camera of the mobile device facing towards the end of the tongue depressor. The examination device is configured to manipulate an oral feature of a mouth while the camera of the mobile device captures an image of the mouth.

20 Claims, 5 Drawing Sheets

DEVICES, SYSTEMS, AND METHODS FOR ORAL AND NON-ORAL EXAMINATION AND DIAGNOSIS

FIELD

The present disclosure generally relates to tools for oral and non-oral examination and diagnosis.

BACKGROUND

Every year millions of people fall ill and suffer from nasal and throat symptoms triggered by flu, cold, bronchitis, pneumonia, strep, and other bacterial and viral infections. A trained doctor may be able to diagnose the patient in part based on his visual observations during an examination. With the right diagnosis, a patient can begin an appropriate treatment plan and get well.

Unfortunately for many, the first step on the road to recovery outlined above begins at a physician's office. Millions of forego the doctor for a myriad of reasons. Some avoid doctors due to financial burden. Others avoid doctors because they don't know how to select one. Some avoid doctors because they don't want to spend the time, or because they are too tough to need one. Many of these people would likely consider treatment if they could avoid the trip to the doctor's office.

Therefore, it would be advantageous to have a simple, non-invasive device that allows for easy diagnosis for various ailments of the throat that could be used by a patient, doctor, or other treatment provider. It would also be advantageous to provide such a device that worked with smartphone or other portable computer device.

SUMMARY

An oral or non-oral examination device for use with a mobile device is provided. The examination device comprises a housing of the examination device configured to removably engage the mobile device, a retention structure mechanically coupled to the housing and defining a slot such a as a rectangular slot, and a tongue depressor retained by the retention structure and having an end extending away from the rectangular slot. A cutaway is defined by a wall of the housing and exposes a camera of the mobile device facing towards the end of the tongue depressor.

In various embodiments, the tongue depressor may be removable coupled to the retention structure. The housing may include a back surface, two opposing side surfaces, and a top surface. The wall defining the cutaway may be located on a rear surface of the housing. The tongue depressor may comprise at least one of wood, plastic, or metal. The housing may comprise a molded plastic. The retention structure may be pivotally coupled to the housing. The retention structure may be substantially parallel to a top surface of the housing. The end of the tongue depressor may be disposed at an angle of up to 30 degrees from orthogonal to a rear surface of the housing. The housing may comprise at least one of a phone case or a partial phone case.

A method of examining a mouth is also provided. The method includes the steps of manipulating an oral feature in the mouth using a tongue depressor extending from a housing coupled to a mobile device, capturing an image of the mouth using a camera of the mobile device exposed from the housing, transmitting the image of the mouth from the mobile device to a remote computing device to request a diagnosis, and receiving the diagnosis from the remote computing device.

In various embodiments, the method may also include the step of analyzing the image locally on the mobile device to determine whether the image meets image quality parameters. The tongue depressor may be retained by a retention structure. The retention structure may be pivotally coupled to the housing. The tongue depressor may be disposed at an angle of up to approximately 30 degrees from orthogonal to a rear surface of the housing. The housing may be removably coupled to the mobile device. The housing may also be, for example, a partial phone case or a full phone case. The housing may be removably coupled to the mobile device by a rear surface, opposing side surfaces, a top surface, and a retention lip that extends over the front of the mobile device.

A computer-based system for diagnosing oral or non-oral ailments is also disclosed herein. The system may include a mobile device having a camera and an examination device removably coupled to the mobile device. The examination device may include a housing configured to engage the mobile device, a retention structure defining a slot and mechanically coupled to the housing, and a tongue depressor retained in the slot of the retention structure and extending away from the housing. The examination device may manipulate an oral feature of a mouth while the camera of the mobile device captures an image of the mouth. In various embodiments, a server may be in electronic communication with the mobile device to receive the image captured by the camera for diagnosis of an oral ailment.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosures, however, may best be obtained by referring to the detailed description and claims when considered in connection with the drawing figures, wherein like numerals denote like elements.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the disclosures, it should be understood that other embodiments may be realized and that logical, chemical, and mechanical changes may be made without departing from the spirit and scope of the disclosures. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Systems, methods and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. After reading the description, it will be apparent to one skilled in the relevant art(s) how to implement the disclosure in alternative embodiments.

Systems, methods, and devices are disclosed herein for oral and non-oral examination and electronic communication between computing devices. As used herein, a "computing device" may refer to any device capable of accepting, storing, and processing data. For, example and without limitation, an electronic device may refer to a smartphone, PDA, laptop, desktop computer, portable phone, GPS device, car navigation system, robot, autonomous drone, or any other suitable device.

Figure 1:
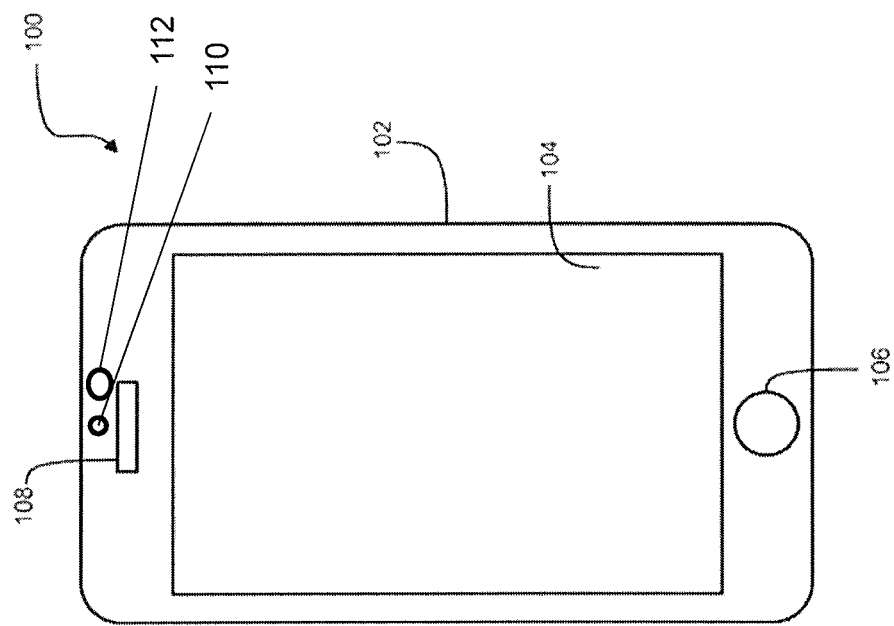
FIG. 1 illustrates a front view of an exemplary computing device for use with an examination device and application according to various embodiments of the disclosure.

With reference to FIG. 1, an exemplary computing device 100 is shown according to various embodiments. Computing device 100 as depicted is a touch screen device such as a smart phone or tablet. Computing device 100 may comprise a housing 102 providing support for various input and output devices. Screen 104 may be a glass display embedded in housing 102 and capable reading touch input. For example, screen 104 may comprise a capacitive touchscreen with a conductor coated over a glass insulator. Computing device 100 may also include an input button 106 and a speaker 108 for an output. The various input and output structures of computing device 100 enable computing device 100 to accept and respond to user input as well as provide visual or audible output.

Computing device 100 may include one or more of the following: a computing system including a processor for processing digital data; a memory coupled to the processor for storing digital data, an input digitizer coupled to the processor for inputting digital data, an application program stored in the memory and accessible by the processor for directing processing of digital data by the processor, a display device coupled to the processor, memory for displaying information derived from digital data processed by the processor, a camera 110 for capturing images, a microphone for capturing sound, and a plurality of databases. Camera 110 may be disposed on a front or back of computing device 100 and may include a flash 112. Various databases used herein may include: oral data; non-oral data; user data; illustrative data; and/or like data useful in the operation of the system. As those skilled in the art will appreciate, the computing device may include an operating system (e.g., Windows, OSX, iOS, UNIX, Linux, MacOS, Android, etc.) as well as various conventional support software and drivers typically associated with computers.

Figure 2:
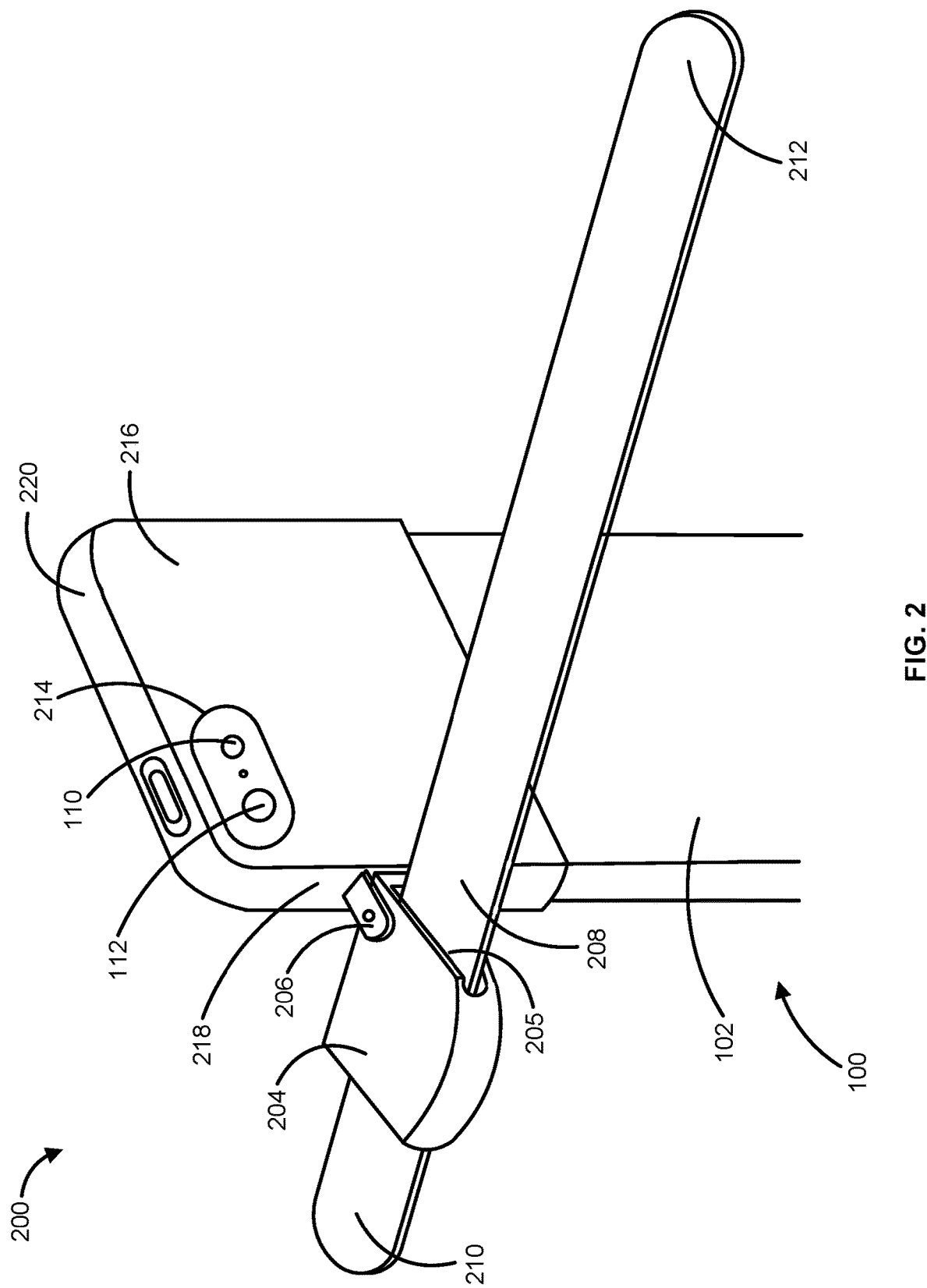
FIG. 2 illustrates a perspective view of an examination device extending from the back of a computing device according to various embodiments of the disclosure.

With reference to FIG. 2, computing device 100 is shown with examination device 200 mechanically coupled to housing 102 of computing device 100, in accordance with various embodiments. Examination device 200 may include a housing 202 defining a cavity that generally matches the external contour of housing 102 of computing device 100. In that regard, housing 202 may be shaped similar to a phone case or a partial phone case. Housing 202 may thus snap or slide into place on computing device 100 in a manner similar to a phone case or partial phone case. Housing 202 may include a back surface 216, opposing side surfaces 218, and a top surface 220. A retention lip 301 (of FIG. 3) may extend over the front surface of mobile device 100 to inhibit housing 202 from slipping off towards the rear of mobile device 100.

In various embodiments, housing 202 may have pivotal joint 206 between housing 202 and retention structure 204. Retention structure 204 may thus pivot about at least one axis relative to housing 202. Retention structure 204 may define a rectangular slot 205 extending through retention structure 204 and suitable for retaining and/or supporting a tongue depressor 208. As used herein, a "tongue depressor" may refer to an elongated medical instrument configured to manipulate, push, probe, depress, handle, or otherwise engage with a portion of a human or non-human body. Housing 202, retention structure 204, and pivotal joint 206 may be made from various materials such as plastics, metals, composite materials, or materials capable of supporting tongue depressor 208 with enough rigidity to depress a tongue or otherwise manipulate oral or non-oral features.

In various embodiments, tongue depressor 208 may include a first end 210 and a second end 212 opposite the first end. Tongue depressor may slide into and partially through slot 205 of retention structure 204. First end 210 of tongue depressor 208 may thus protrude from a first side of slot 205 and the second end 212 of tongue depressor 208 may extend through a second side of slot 205 opposite the first side. Tongue depressor may extend from retention structure 204 at an angle relative to housing 104 of mobile device 100. For example, tongue depressor may be oriented at a plane orthogonal to the rear surface of mobile device 100. Tongue depressor may also be oriented on a plane ranging from +/−10 degrees, +/−20 degrees, or +/−30 degrees from orthogonal to the rear surface of mobile device 100. The foregoing angles are provided for exemplary purposes and not intended to limit potential mounting arrangements between tongue depressor 208 and mobile device 100.

In various embodiments, the second end 212 of tongue depressor 208 may protrude further from retention structure 204 than the first end 210. In that regard, the second end 212 may be suitable for depressing a tongue, an anal or gynecological orifice, or otherwise manipulating oral or non-oral features at a distance suitable for capturing an image using camera 110 and/or flash 112. Tongue depressor may be an elongated, flat stick made of wood, metal, plastic, rubber, and/or other suitable materials having enough rigidity to depress a tongue or otherwise manipulate oral or non-oral features.

In various embodiments, housing 202 may include a cutaway defined by wall 214. The cutaway defined by wall 214 may expose camera 110 and/or flash 112 from housing 202 so camera 110 can operate to photograph a mouth and/or various oral or non-oral features. Housing 202, wall 214, and a portion of pivotal joint 206 may be molded, for example, as an integral component.

Figure 3:
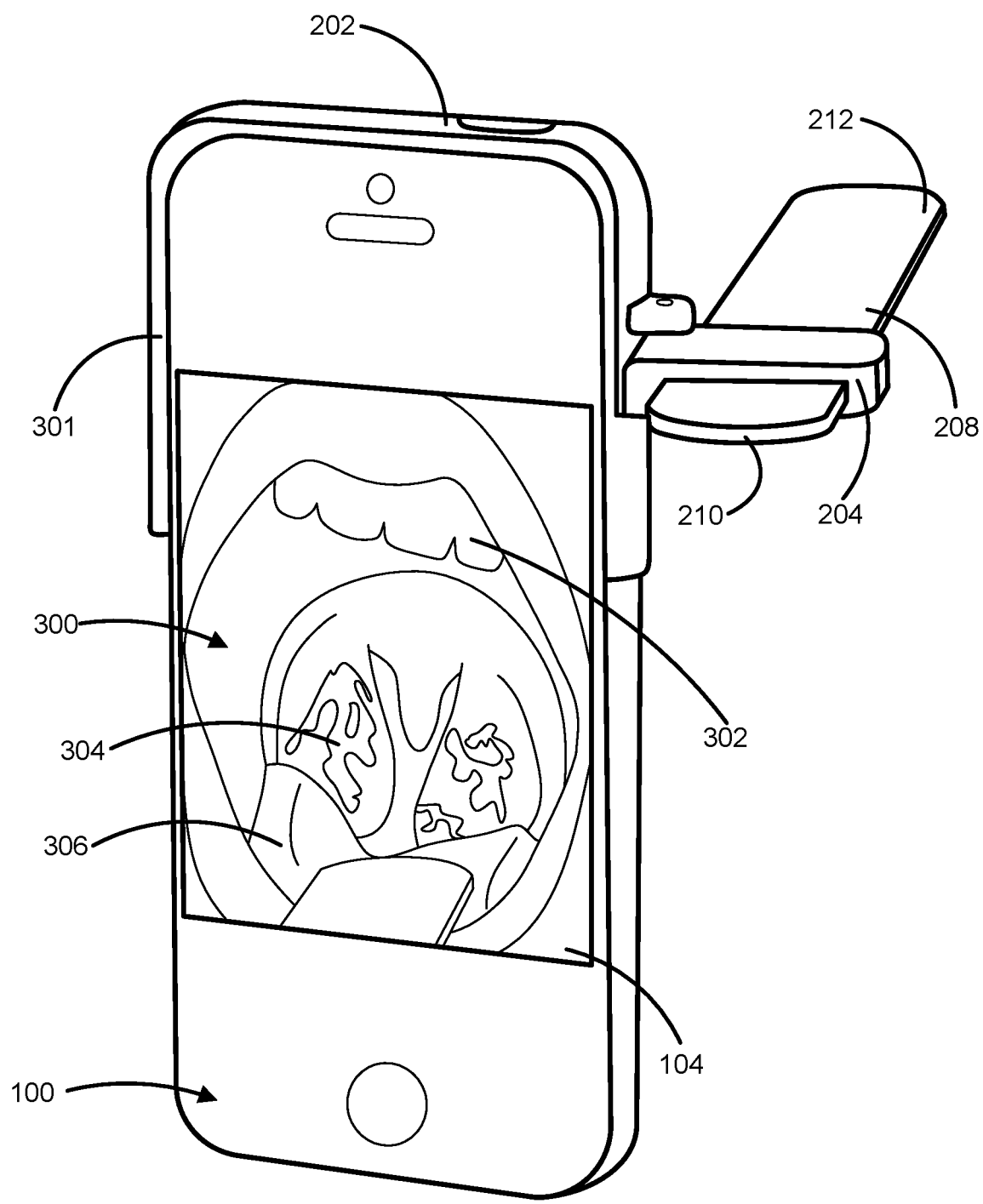
FIG. 3 illustrates a perspective view of an examination device extending away from the front of a computing device configured to capture an image according to various embodiments of the disclosure.

FIG. 3 illustrates a front view of computing device 100 mechanically coupled to examination device 200, in accordance with various embodiments. Screen 104 of mobile device 100 is capturing an image of mouth 300 and features thereof. Tongue depressor 208 is shown in the image with second end 212 in contact with and manipulating tongue 306, Teeth 302 and throat 304 may also be visible and subject to visual examination on the image of mouth 300. Tongue depressor 208 and retention structure 204 may pivot relative to housing 202 to vary the angle at which camera 110 (of FIG. 2) captures an image of mouth 300 and tongue depressor 208. Images may be captured using any digital image format suitable for storage, viewing, and/or transmission over a network.

Figure 4:
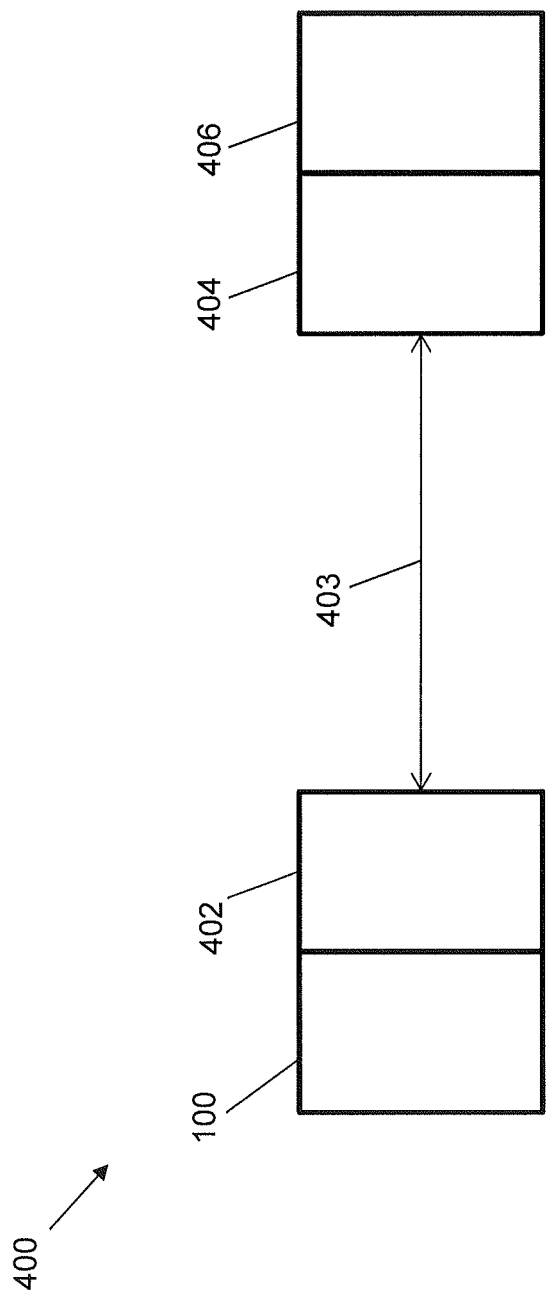
FIG. 4 illustrates a diagnosis system with computing device in electronic communication over a network according to various embodiments of the disclosure.

Referring now to FIG. 4, an exemplary system 400 for diagnosing oral or non-oral ailments is shown according to various embodiments. System 400 may include mobile device 100 running application 402. Application 402 may be a native application written to run on the operating system of mobile device 100. Application 402 may also be a web application executed on mobile device 100 using a web browser. In that regard, application 402 may be device specific or device agnostic without altering the general functionality of system 400. Application 402 may provide a graphical interface for a user to capture images and/or transmit images across network 403 to application services 404 running on server 406. One such exemplary application 402 is the eNcounter® mobile app developed and licensed by Global Media Group, LLC of Scottsdale, Ariz.

In various embodiments, server 406 may be any computing device described herein, or any other computing device capable of sending and receiving application data across network 403 and otherwise supporting the operation of application 402 running on mobile device 100. Although server 406 uses the singular term "server," in various embodiments server 406 may be multiple computing device operating to support application 402. For example, server 406 may include one or more rack-mounted server, computer, smartphone, PDA, laptop, desktop computer, computing cluster, distributed file system, load balancing system, or any other suitable computing devices in communication with one another and providing back end support to application 402.

In various embodiments, physicians may also run an application, such as the eNcounter™ application, interacting with application services 404 to view images captured by mobile devices 100. Physicians may make diagnosis based on features captured in the images. In various embodiments, application services 404 may also run optical recognition against the oral images to automatically diagnose oral ailments based on a set of rules. Physicians may review and confirm machine diagnosis to ensure accuracy. Physicians may also provide suitable prescriptions to combat any oral ailments detected by visual examination.

Figure 5:
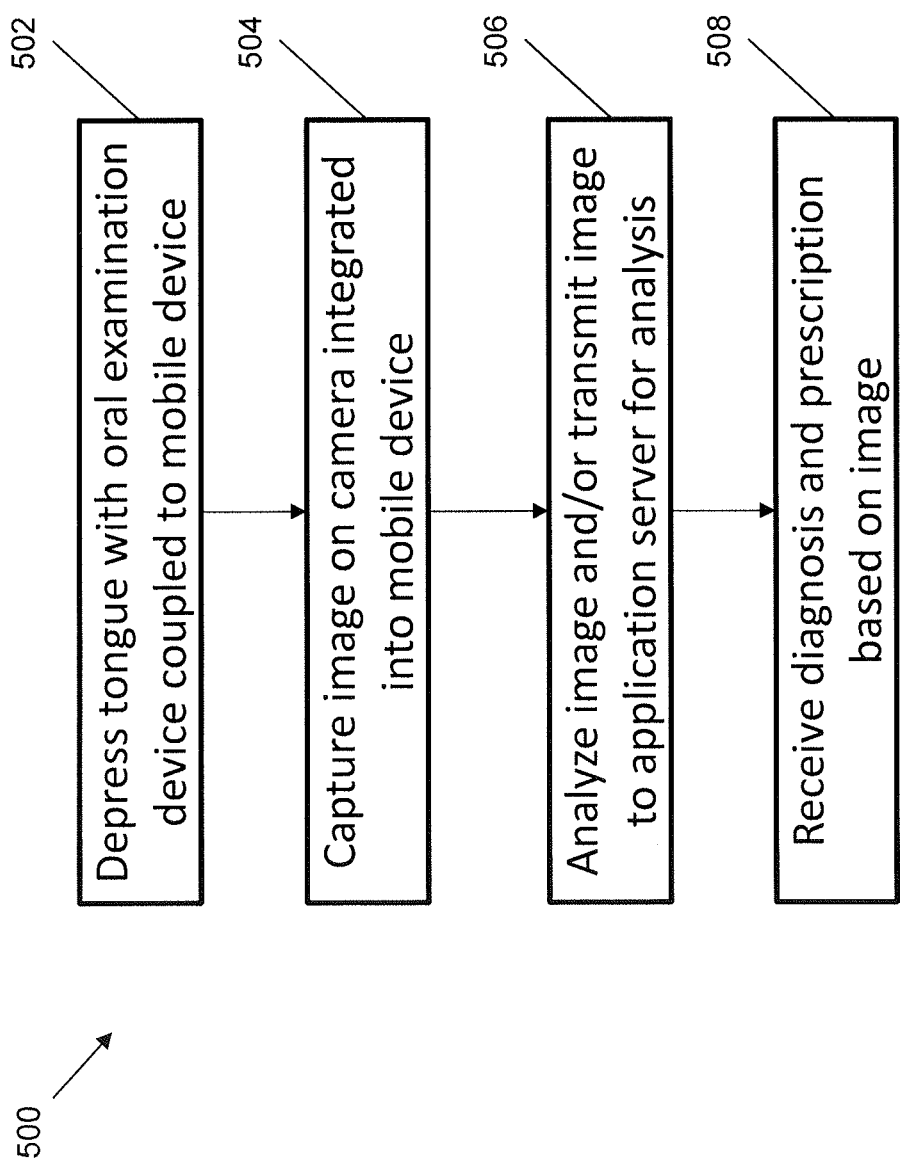
FIG. 5 illustrates an exemplary process for using an examination device in concert with a computing device to capture examination data according to various embodiments of the disclosure.

Referring now to FIG. 5, process 500 for remote diagnosis of oral ailments is shown for execution on system 400. Tongue depressor 208 of examination device 200 coupled to mobile device 100 may depress a tongue or otherwise manipulate oral features (Step 502). The tongue depressor 208 may press against the tongue at second end 212 when used with a rear-facing camera on a mobile device. For use with a front facing phone, tongue depressor 208 may be pulled towards first end 210 and first end 210 of tongue depressor 208 may engage and/or manipulate the tongue or other oral features. Depressing the tongue may enhance exposure of the throat to camera 110 and/or flash 112 of mobile device 100.

In various embodiments, mobile device 100 may capture an image of the mouth using camera 110 (Step 504). The image may capture the mouth and its features for review and diagnosis. Flash 112 may assist in capturing an image with adequate lighting for review. The image may be captured and stored through an interface displayed by application 402 running on mobile device 100.

In various embodiments, application 402 may analyze the image locally and/or transmit the image to serve 406 for analysis (Step 506). Analysis executed locally by application 402 may, for example, evaluate whether the image meets image quality parameters. For example, image quality parameters may include whether the image displays a mouth and throat, whether lighting is sufficient for diagnosis, whether the angle is suitable for diagnosis, or other image quality criteria. Analysis executed locally may also include generating an estimated diagnosis or identifying symptoms visible in the image. In that regard, mobile device 100 and application 402 may capture an image and provide some form of diagnosis to a user without contacting server 406 in various embodiments.

As described above, server 406 may also receive the image from mobile device 100 and perform analysis remotely from mobile device 100. For example, server 406 may store the image for review by a trained physician as described above. The physician may then make a diagnosis, request further imaging, request further communication from the patient, and/or generate a prescription for the patient. The patient may thus receive a diagnosis and/or prescription based on the image captured by application 402 running on mobile device 100 (Step 508). Process 500 and system 400 enable patients to receive diagnosis information remotely without physically stepping into a doctor's office. Patients can thus avoid long wait times and other ill individuals that are typically present in a doctor's office. Physicians may also interact with a greater number of patients in a shorter time period as the patients need not be staged in a room at the office and be subject to various in-person examinations.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosures.

The scope of the disclosures is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly, listed or inherent to such process, method, article, or apparatus.

What is claimed is:

1. An examination device for use with a mobile device, comprising:
    a housing of the examination device configured to removably engage the mobile device;
    a retention structure mechanically coupled to the housing and defining a slot;
    a tongue depressor retained by the retention structure and having an end extending away from the slot; and
    a cutaway defined by a wall of the housing and configured to expose a camera of the mobile device facing towards the end of the tongue depressor.

2. The examination device of claim 1, wherein the tongue depressor is removably coupled to the retention structure.

3. The examination device of claim 1, wherein the housing comprises a back surface, two opposing side surfaces, and a top surface.

4. The examination device of claim 1, wherein the wall defining the cutaway is disposed on a rear surface of the housing.

5. The examination device of claim 1, wherein the tongue depressor comprises at least one of wood, plastic, or metal.

6. The examination device of claim 1, wherein the housing comprises a molded plastic.

7. The examination device of claim 1, wherein the retention structure is pivotally coupled to the housing.

8. The examination device of claim 7, wherein the retention structure is substantially parallel to a top surface of the housing.

9. The examination device of claim 1, wherein the end of the tongue depressor is disposed at an angle of up to 30 degrees from orthogonal to a rear surface of the housing.

10. The examination device of claim 1, wherein the housing comprises at least one of a phone case or a partial phone case.

11. A method of examining a mouth, comprising:
    manipulating an oral feature in the mouth using a tongue depressor extending from a housing coupled to a mobile device;
    capturing an image of the mouth using a camera of the mobile device exposed from the housing;
    transmitting the image of the mouth from the mobile device to a remote computing device to request a diagnosis; and
    receiving the diagnosis from the remote computing device.

12. The method of claim 11, further comprising analyzing the image locally on the mobile device to determine whether the image meets image quality parameters.

13. The method of claim 11, wherein the tongue depressor is retained by a retention structure.

14. The method of claim 13, wherein the retention structure is pivotally coupled to the housing.

15. The method of claim 14, wherein the tongue depressor is disposed at an angle of up to 30 degrees from orthogonal to a rear surface of the housing.

16. The method of claim 11, further comprising removably coupling the housing to the mobile device.

17. The method of claim 16, wherein the housing comprises at least one of a partial phone case or a phone case.

18. The method of claim 16, wherein the housing is removably coupled to the mobile device by a rear surface, opposing side surfaces, a top surface, and a retention lip that extends over a front surface of the mobile device.

19. A computer-based system, comprising:
    a mobile device having a camera; and
    an examination device removably coupled to the mobile device, the examination device comprising:
        a housing configured to engage the mobile device;
        a retention structure defining a slot and mechanically coupled to the housing; and
        a tongue depressor retained in the slot of the retention structure and extending away from the housing,
    wherein the examination device is configured to manipulate an oral feature of a mouth while the camera of the mobile device captures an image of the mouth.

20. The computer-based system of claim 19, further comprising a server in electronic communication with the mobile device and configured to receive the image captured by the camera to diagnose an oral ailment.

* * * * *